(12) United States Patent
Schneider et al.

(10) Patent No.: US 6,276,191 B1
(45) Date of Patent: Aug. 21, 2001

(54) OXYGEN SENSOR

(75) Inventors: Jens Stefan Schneider, Anderson, SC (US); Harald Neumann, Vaihingen (DE); Frank Stanglmeier, Moeglingen (DE); Bernd Schumann, Rutesheim (DE); Thomas Moser, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/356,819

(22) Filed: Jul. 19, 1999

(30) Foreign Application Priority Data

Jul. 16, 1998 (DE) .................................. 198 32 098

(51) Int. Cl.[7] .................. G01N 27/00; G01N 27/409; G01N 33/00
(52) U.S. Cl. .................. 73/23.31; 73/23.32; 73/31.05; 422/90; 422/94; 204/426
(58) Field of Search ........................ 73/23.2, 23.31, 73/31.05, 23.32, 118.1; 338/34, 38; 422/88, 94; 204/426, 424, 427

(56) References Cited

U.S. PATENT DOCUMENTS

| | | | |
|---|---|---|---|
| 4,911,892 | * | 3/1990 | Grace et al. ............ 422/94 |
| 5,512,882 | * | 4/1996 | Stetter et al. ............ 340/632 |
| 5,531,879 | | 7/1996 | Zanini-Fisher et al. ...... 204/427 |
| 5,635,627 | * | 6/1997 | Bytyn .................... 73/31.05 |
| 5,635,628 | * | 6/1997 | Fleischer et al. ........... 73/31.06 |
| 5,668,301 | * | 9/1997 | Hunter .................... 73/23.2 |
| 5,698,771 | * | 12/1997 | Shields et al. ............ 73/31.05 |
| 5,747,669 | * | 5/1998 | Suzuki ................... 73/23.21 |
| 5,814,281 | * | 9/1998 | Williams et al. ........... 422/88 |
| 5,824,271 | * | 10/1998 | Frank et al. .............. 422/98 |
| 5,827,415 | * | 10/1998 | Gür et al. ................ 204/426 |
| 5,969,231 | * | 10/1999 | Qu et al. ................. 73/31.05 |
| 5,970,780 | * | 10/1999 | Mori ..................... 73/23.31 |

FOREIGN PATENT DOCUMENTS 29 35 196    3/1981    (DE) .

* cited by examiner

Primary Examiner—Daniel S. Larkin
Assistant Examiner—David J. Wiggins
(74) Attorney, Agent, or Firm—Kenyon & Kenyon

(57) ABSTRACT

An oxygen sensor for determining the oxygen concentration in the exhaust gas flow of an internal combustion engine. The sensor includes an outer electrode exposed to the exhaust side and a reference electrode exposed to the ambient air. In the sensor, a space adjacent to the reference electrode or surrounding the reference electrode has an adsorbing and/or absorbing agent, which is introduced, for example, in a loose powder packing or a multiple pellet packing. Other versions of the novel oxygen sensor also have an oxygen supplying material, such as, for example, Mn-oxide, Ba-oxide and/or Ce-oxide, to help promote combustion of exhaust gas components/pollutants and any residue chemicals left remaining from the sensor manufacturing process.

9 Claims, 1 Drawing Sheet

OXYGEN SENSOR

FIELD OF THE INVENTION

The present invention relates to an oxygen sensor for determining the oxygen concentration in the exhaust gas flow of an internal combustion engine, in which the sensor includes an outer electrode exposed to the exhaust side and a reference electrode exposed to a reference atmosphere or to the ambient air.

BACKGROUND INFORMATION

An oxygen sensor is described, by way of example, in U.S. Pat. No. 5,531,879. In an oxygen sensor of this type, used as a λ-probe, there exists the problem that, when the oxygen sensor heats up, the sensor characteristic curve shifts due to humidity, penetrating exhaust, or residues in or on the housing or mounting parts on the reference side. This phenomenon, known as CSD behavior (Characteristic Shift Down), is treated in the oxygen sensor proposed in the above-referenced U.S. patent by employing for the reference electrode a metal, e.g., gold or a gold-platinum alloy, that is not catalytically active.

In other oxygen sensors of the related art, the CSD behavior is avoided either by the reference side being completely sealed off from the exhaust side, or by an active Pt or Pt/Pd electrode or component parts on the reference side being heated. All of the known measures in the related art for avoiding the CSD problem are either complicated or expensive.

SUMMARY OF THE INVENTION

An object of the present invention is to provide an oxygen sensor that is suitable for use as a λ-probe in a motor vehicle, in which the CSD problem is solved by a simple and cost-effective means.

The above object is achieved in accordance with a first preferred aspect of the present invention in that a space surrounding the reference electrode or a space adjacent to the reference electrode has an adsorbing agent and/or an absorbing agent. The adsorbing/absorbing agent that is used can be applied either in the form of a loose powder packing, in the form of pellets, as rings or as an intermediate layer in a packing or on other suitable mounting locations on the reference side.

An adsorbing/absorbing material of this type, given sufficient temperature stability, is able to take up and to bind $H_2O$, CO, hydrocarbons, etc., penetrating on the reference side.

Zeolites are particularly suited as an adsorbing/absorbing material. Zeolites have proven to be particularly suited technically, in many respects, as adsorption/absorption agents based on their particularly large interior hollow spaces, which are accessible via pore openings that are of equal size.

The advantage of an oxygen sensor according to the present invention that is realized by the introduction of zeolite material is particularly to be found in the fact that the reference electrode can also be made of a catalytically active metal.

A second oxygen sensor realized in accordance with the present invention is characterized in that the reference electrode or the reference-side mounting parts have at least one material that supplies on the reference side additional oxygen for the combustion of exhaust that has penetrated or of residues from the manufacturing process.

Preferred examples of such materials are Mn-oxide, Ba-oxide, or Ce-oxide, which, e.g., can be employed as a solution, as pellets, or as paste components. The measure proposed in accordance with the second preferred aspect, to provide the reference electrode or reference-side mounting parts with at least one material that supplies on the reference side additional oxygen for the combustion of exhaust that has penetrated or residues from the manufacturing process, can be combined particularly usefully with the proposed introduction or building up of an absorber/adsorber material. Thus an oxygen sensor realized according to the present invention avoids CSD effects that are caused by the manufacturing process and/or the operation or design.

DETAILED DESCRIPTION

Figure 1:
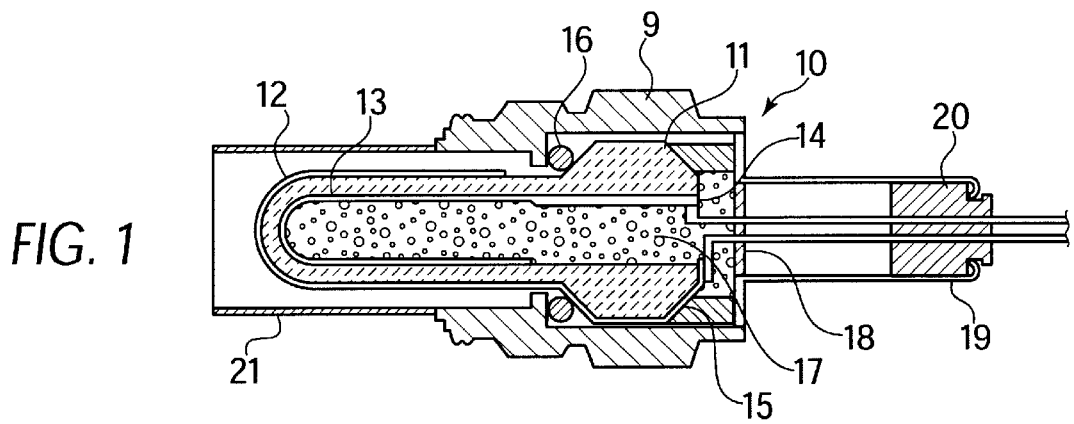
FIG. 1, in the form of a schematic longitudinal section, depicts a first specific embodiment of an oxygen sensor according to the present invention having adsorber/absorder material in the form of a loose powder packing or in the form of pellets.

The exemplary embodiments according to the present invention designated generally by number 10, and depicted in FIGS. 1 through 4 in the form of schematic longitudinal sections, have the following features in common:

A cylindrical ceramic body 11, on the outer side of its exhaust-side end exposed to the exhaust side, has an external electrode 12 made of a catalytic precious metal, such as platinum. On the inner side of cylindrical ceramic tube 11 is situated a reference or interior electrode 13 (FIGS. 1–3) (or 23 from the modified material; FIG. 4). On the terminal side, outer electrode 12 is connected via a connection terminal 15 to a connection lead that is not designated in greater detail, whereas the reference or inner electrode, 13 or 23, respectively, is connected via a second connection terminal 14 or 25, respectively, to a further connecting lead that is not designated in greater detail. The connecting leads are run via a sleeve 20 on the terminal-side end of the oxygen sensor. An essentially cylindrical outer housing 9, which can be configured, for example, in the form of a spark plug screw base, acts to stabilize oxygen sensor 10 mechanically, as well as to insert the sensor into a suitable (undepicted) receiving ring in the exhaust pipe. A protective tube 21, open on the exhaust side, surrounds the end of oxygen sensor 10 that extends into the exhaust pipe, and the terminal-side end is situated inside a metallic sleeve 19 that is connected to outer housing 9, through whose end the electrical connecting leads run. Receiving ring 16 rests in outer housing 9, the ring 16 sealing off the exhaust side from the reference side.

In FIG. 1, the adsorber/absorber material preferably composed of zeolite, in the form of a loose powder packing 17 or in the form of pellets, is introduced into the space adjacent to reference electrode 13. The space is closed off to the connection side by an air-permeable ring 18.

Figure 2:
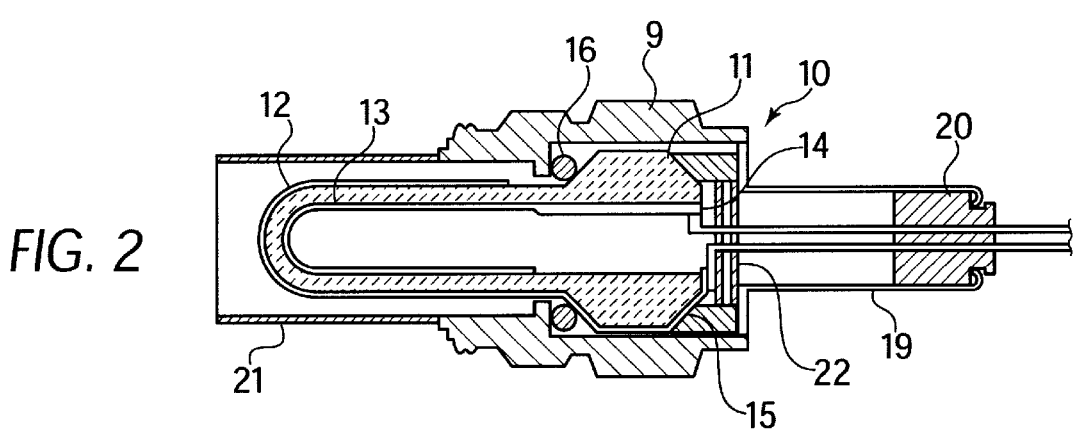
FIG. 2 depicts a second embodiment of an oxygen sensor according to the present invention, in which zeolite is introduced in the form of rings.

In FIG. 2, an adsorber/absorber material made preferably of zeolite is introduced in the form of two rings 22 bordering on the space adjacent to reference electrode 13.

Figure 3:
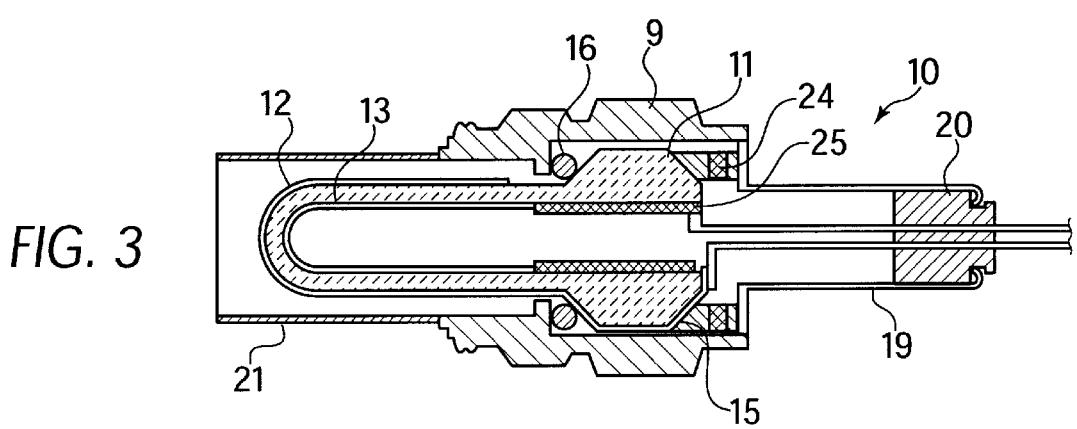
FIG. 3 depicts a third embodiment of an oxygen sensor according to the present invention, in which zeolite is introduced in combined form as an interior ring in a ceramic body and as an intermediate layer in a packing.
Figure 4:
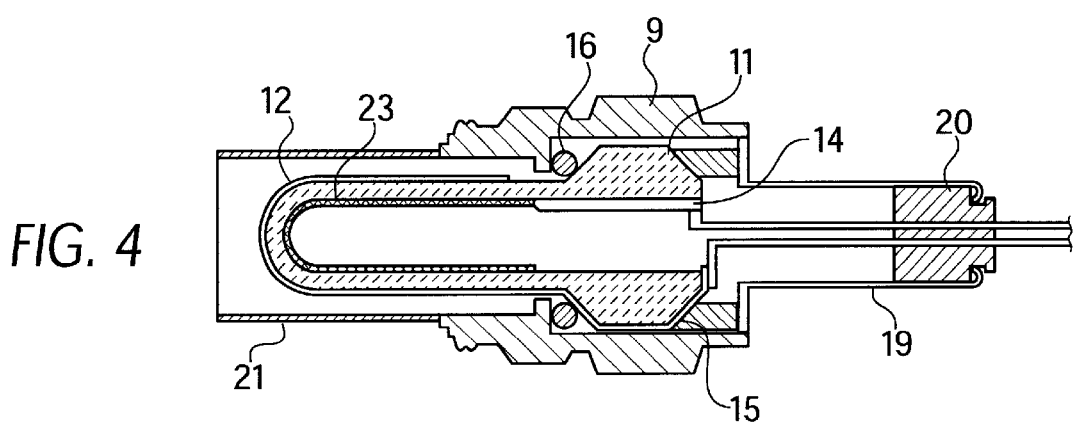
FIG. 4 depicts a fourth exemplary embodiment of an oxygen sensor according to the present invention, in which the reference and inner electrode contain a material that supplies on the reference side additional oxygen for the combustion of exhaust that has penetrated or of residues from the manufacturing process.

The embodiment of the oxygen sensor according to the present invention depicted in FIG. 3 has a combination of a ring adjacent to reference electrode 13 and to an intermediate layer 24 of a packing that is not depicted in greater detail.

The exemplary embodiment depicted in FIG. 4 has a modified interior electrode 23, which supplies on the reference side additional oxygen for the combustion of exhaust that has penetrated or residues from the manufacture process. The material of the modified interior electrode can be made of Co-oxide, Pr-oxide, or Tb-oxide, but preferably of Mn-oxide, Ba-oxide or Ce-oxide, and it can be applied to the interior electrode in the form of a solution, pellets, or paste. The oxides listed here are in each case oxygen-rich forms, which are reduced then to an oxygen-poor oxide:

e.g. $CeO_2 \rightarrow Ce_2O_3$ or $BaO_2 \rightarrow BaO$ or $Co_2O_3 \rightarrow CoO$ As mentioned above, the exemplary embodiment depicted in FIG. 4 can also be combined with the exemplary embodiments depicted in FIGS. 1–3, i.e., provision can also be made for an interior electrode 23, preferably modified using Mn-oxide, Ba-oxide, or Ce-oxide, and also, e.g., a zeolite powder packing in accordance with FIG. 1. In conclusion, the features in accordance with FIGS. 1–3 can be combined with each other.

What is claimed is:

1. An oxygen sensor for determining an oxygen concentration in an exhaust flow of an internal combustion engine, comprising:

an external electrode exposed to an exhaust side;

a reference electrode exposed to one of a reference atmosphere and an ambient air, the reference electrode being disposed on a reference side that is isolated from the exhaust side; and a material including at least one of an adsorbing agent and an absorbing agent and being provided in one of a space adjacent to the reference electrode and a space surrounding the reference electrode, the material being able to at least one of take up and bind with at least one of $H_2O$, CO and a hydrocarbon penetrating from the exhaust side into the one of the reference atmosphere and the ambient air on the reference side.

2. The oxygen sensor according to claim 1, wherein the at least one of the adsorbing agent and the absorbing agent is introduced as a loose powder packing.

3. The oxygen sensor according to claim 1, wherein the at least one of the adsorbing agent and the absorbing agent is introduced as pellets.

4. The oxygen sensor according to claim 1, wherein the at least one of the adsorbing agent and the absorbing agent is introduced as at least one ring.

5. The oxygen sensor according to claim 1, wherein the at least one of the adsorbing agent and the absorbing agent is introduced as an intermediate layer in a packing which seals off the exhaust side from the reference side.

6. The oxygen sensor according to claim 1, wherein the at least one of the adsorbing agent and the absorbing agent includes a zeolite material.

7. The oxygen sensor according to claim 1, further comprising:

a plurality of reference-side mounting parts, wherein one of the reference electrode and the plurality of reference-side mounting parts includes at least one material that supplies additional oxygen for a combustion of one of an exhaust that has penetrated and residues from a manufacturing process.

8. An oxygen sensor for determining an oxygen concentration in an exhaust gas flow of an internal combustion engine, comprising:

an external electrode exposed to an exhaust side;

a reference electrode exposed to one of a reference atmosphere and an ambient air;

a material including at least one of an adsorbing agent and an absorbing agent and being provided in one of a space adjacent to the reference electrode and a space surrounding the reference electrode; and a plurality of reference-side mounting parts;

wherein one of the reference electrode and the plurality of reference-side mounting parts includes at least one material that supplies additional oxygen for a combustion of one of an exhaust that has penetrated and residues from a manufacturing process; and wherein the at least one material that supplies the additional oxygen includes at least one of Mn-oxide, Ba-oxide, and Ce-oxide.

9. An oxygen sensor for determining an oxygen concentration in an exhaust flow of an internal combustion engine, comprising:

an external electrode exposed to an exhaust side;

a reference electrode exposed to one of a reference atmosphere and an ambient air;

a material including at least one of an adsorbing agent and an absorbing agent and being provided in one of a space adjacent to the reference electrode and a space surrounding the reference electrode; and a plurality of reference-side mounting parts;

wherein one of the reference electrode and the plurality of reference-side mounting parts includes at least one material that supplies additional oxygen for a combustion of one of an exhaust that has penetrated and residues from a manufacturing process; and wherein the at least one material that supplies the additional oxygen is introduced as one of a solution, a plurality of pellets, and as a paste.

* * * * *